United States Patent [19]

Pickford

[11] Patent Number: 5,391,545
[45] Date of Patent: *Feb. 21, 1995

[54] COMBATING OF UNDESIRED ORGANISMS

[75] Inventor: Robert J. J. Pickford, North Humberside, England

[73] Assignees: Aquaspersions Limited, West Yorkshire; Humber Growers Marketing Organisation Limited, North Humberside, both of United Kingdom

[*] Notice: The portion of the term of this patent subsequent to Aug. 18, 2009 has been disclaimed.

[21] Appl. No.: 997,308

[22] Filed: Dec. 23, 1992

Related U.S. Application Data

[63] Continuation-in-part of Ser. No. 890,224, May 29, 1992, abandoned, which is a continuation of Ser. No. 634,189, Jul. 12, 1989, Pat. No. 5,140,017.

[30] Foreign Application Priority Data

Jul. 12, 1988 [GB] United Kingdom ............ 8816542
May 22, 1989 [GB] United Kingdom ............ 8911744

[51] Int. Cl.$^6$ .......... A61K 9/34; A01N 25/34; B01J 13/02; C12N 11/10
[52] U.S. Cl. ............... 514/58; 424/405; 424/407; 424/410; 47/DIG. 11
[58] Field of Search .......... 514/58, 60; 536/103; 424/405, 407, 410; 47/DIG. 11

[56] References Cited

U.S. PATENT DOCUMENTS 4,888,325  12/1989  Schroeder et al. ............ 424/405
5,140,017   8/1992  Pickford ....................... 514/58

Primary Examiner—Ronald W. Griffin
Attorney, Agent, or Firm—Nixon & Vanderhye

[57] ABSTRACT

Undesired organisms, including insects, mites and fungi, may be combated by application of a liquid composition which comprises starch dextrin or an analogous derivative of amylopectin as an active ingredient. The aforementioned active ingredients may be used as the sole active ingredient or in combination with other active ingredients. Examples of undesired organisms which have been found to be affected are whiteflies, thrips, red spider mites, broadmites, cucumber powdery mildew and oat powdery mildew.

13 Claims, No Drawings

COMBATING OF UNDESIRED ORGANISMS

This application is a continuation-in-part application of application Ser. No. 07/890,224, filed May 29, 1992, now abandoned, which is a Rule 60 continuation of U.S. application Ser. No. 07/634,189, filed Jul. 12, 1989, now U.S. Pat. No. 5,140,017.

This invention relates to the combating of undesired organisms and is concerned particularly, although not exclusively, with the combating of insects, mites and fungi.

Chemical methods of controlling undesired organisms are well known. However, organisms have an ability to evolve, so that after a period of time their resistance to a particular chemical tends to increase. Accordingly, new pesticides must continually be developed so that man is always at least one step ahead of the pests-always having a pesticide to which the target pest has not yet become resistant.

Another consideration when developing a pesticide, besides the toxicity to the target organism, is whether the pesticide will have detrimental effects on desirable organisms. Thus, before a new pesticide can be marketed, stringent tests must be carried out to ascertain its safety in the eco-system and the environment as a whole.

It is an object of the present invention, to provide an improved pesticide.

According to a first aspect of the present invention, there is provided a method of treatment of a plant to combat an undesired insect, mite or fungal organism which is infecting the plant or may subsequently infect the plant, comprising the step of foliar application of a liquid composition comprising, as an active ingredient, a dextrinised starch material.

A dextrinised starch material may be a dextrinised starch or an analogous derivative of amylopectin. The preferred dextrinised starch material is dextrinised starch.

The dextrinised starch material may be the sole active ingredient in the liquid composition. Alternatively, the liquid composition may include one or more further active ingredients. Such a further active ingredient may be natural or synthetic. A preferred further active ingredient is synthetic.

Whilst a useful method in accordance with the present invention employs a dextrinised starch or analogous derivative of amylopectin, it may be desirable to employ said one or more further active ingredients in order to provide extended or enhanced activity. Methods in accordance with the present invention which employ a dextrinised starch or an analogous derivative of amylopectin and a further active ingredient have shown levels of efficiency enhanced by synergistic interaction between the active ingredients. Further, the employment of said one or more further active ingredients may be of benefit because of a broader range of pests which are combated, whether synergism is shown or not.

Suitable further active ingredients include TORQUE (Trade Mark for hexakis (2-methyl-2-phenylpropyl)distannoxane), RUBIGAN (Trade Mark for alpha-(2-chlorophenyl)-alpha-(4-chlorophenyl)-5-pyrimidinemethanol) and AFUGAN (Trade Mark for 2-((Diethoxyphosphinothioyl)oxy)-5-methylpyrazolo(1,5-a)pyrimidine-6-carboxylic acid ethyl ester. Other further active ingredients include Fungaflor (Trade Mark for imazalil; i.e. allyl 1-(2,4-dichlorophenyl)-2-imidazol-1-ylethyl ether), Nimrod (Trade Mark for Bupirimate; i.e. 5-butyl-2-ethylamino-6-methyl (pyrimidin-4-yl dimethylsulfamate), chlorothalonil (i.e. tetrachloroisophthalonitrile) and verticillium lecanni.

Dextrinised starch is commonly called a starch-dextrin, or simply a dextrin. It is commonly defined as an intermediate product or products in the transformation of starch into maltose or D-glucose.

Dextrinisation may take place by one of various methods, including enzymic reaction, in particular by amylases on starch; by the action of *Bacillus Macerans*, to yield cyclic dextrins having six and seven D-glucose units; by acid hydrolysis in aqueous media; and by the action of heat with or without acid being present, on starch. The latter dextrins, sometimes called pyrodextrins, are especially preferred dextrins for use in the method of the invention.

Pyrodextrins are commonly made by spraying dried starch with an acid, typically a mineral acid, usually hydrochloric acid but sometimes nitric acid, then drying the sprayed starch to leave a 1–5% water content. The acidified starch is hydrolysed and reverted by heating. At a final temperature of 95°–120° C., a white pyrodextrin is produced, typically having a low ratio of branched derivatives. At a final temperature of 150°–180° C., a canary-yellow dextrin is produced, having a higher degree of branching, approximately 20%, and being less viscous, than the white dextrins. Without acid but with a longer reaction time and a final temperature of 170°–195° C., the product is a British gum dextrin. Following the final heating step, cooling is rapid to prevent over-conversion. The acid may be neutralised at this point in the process if required.

In the present invention, the use of canary-yellow dextrins is particularly preferred.

For the dextrinised starch material, starch or a starch derivative of any origin may be employed, for example a starch or starch derivative derived from tubers, such as potato, or derived from cereals, such as corn or rice. Very interesting activity has been observed with pyrodextrins derived from such potato starch.

The dextrinised starch material may be synthetic or natural, although natural active ingredients are likely to be used, for economic reasons.

Starch comprises amylopectin and amylose. Only the amylopectin dextrinises under the conditions described above.

The area to which the composition is applied may be already infected with a target organism or subject to or at risk of such infection, the treatment of the area then being prophylactic. The dosage of dextrinised starch material used may, for example, be from about 3 to about 1150 kg/ha, suitably about 50–150 kg/ha. The dosage of further active ingredients may suitably be in the range 0.02 to 500 kg/ha.

A carrier in a composition used in a method according to the invention is any material with which the active ingredient is formulated to facilitate application to the area to be treated, or to facilitate storage, transport or handling. A carrier may be a solid or a liquid, including a material which is normally gaseous but which has been compressed to form a liquid, and any of the carriers normally used in formulating biocidal compositions may be used.

Agricultural compositions are often formulated and transported in a concentrated form which is subsequently diluted by the user before application. The presence of small amounts of a carrier which is a surface-active agent facilitates this process of dilution. Thus, preferably at least one carrier in a composition used in the method of the invention is a surface-active agent. For example the composition may contain at least two carriers, at least one of which is a surface-active agent.

It is preferred that a surface active agent is provided to facilitate wetting, particularly if the solution is a colloidal solution. Aqueous solutions are preferred.

A surface active agent may be an emulsifying agent, a dispersing agent or a wetting agent; it may be nonionic or ionic. Examples of suitable surface active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenyl or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; polymers of ethylene oxide and copolymers of ethylene oxide and propylene oxide; and alkali metal salts of fatty acids containing at least 10 carbon atoms.

Preferred wetting agents are the alkali metal salts of fatty acids containing at least 10 carbon atoms, for example sodium laurate, and condensation products of alkyl phenols with ethylene oxide and/or propylene oxide, for example nonyl phenyl ethylene oxide condensate.

The combination of an active ingredient and a wetting agent is thought to be particularly important in obtaining an effective liquid composition.

Suitably, a liquid composition comprises about 0.05–5 wt. %, preferably about 0.1–3 wt. %, of wetting agent(s).

The presence of a preservative to prevent degradation or spoiling of an active ingredient as described above is thought to be important. Small amounts of a preservative, for example about 0.001 to 1 wt. %, in particular about 0.01 to 0.5 wt. %, based on the liquid composition to be applied to the area, may be suitable.

A preferred liquid composition to be applied comprises about 0.01 to 50 wt. % of dextrinised starch material; about 0.05 to 5 wt. % wetting agent, and about 0.001 to 1 wt. % preservative; and optionally from 0.0001 to 25 wt. %.

A particularly preferred liquid composition to be applied comprises about 0.1 to 10 wt. % of dextrinised starch material; about 0.1 to 3 wt. % wetting agent; about 0.1 to 1 wt. % preservative; and 0.005 to 10 wt. % of a further active ingredient.

Suitably, the composition may contain at least about 0.01% by weight of dextrinised starch material, suitably about 0.1 to 50%. Preferably, the composition contains about 0.1 to 10% by weight of dextrinised starch material.

Most preferably, the composition contains about 0.1 to 5% by weight of dextrinised starch material. Especially preferred is a composition containing about 0.1 to 3% by weight of dextrinised starch material, especially about 0.1 to 2%.

The liquid composition may include a salt, so provided in order to affect the osmotic pressure or diffusion gradient between the organism and its surroundings.

In living systems, it is often found that the pH of solutions is important. Accordingly, it may be desirable to buffer the composition in order to maintain it at a generally constant pH.

The target organisms may be insects. The composition may be applied to insect eggs. Alternatively, the composition may be applied whilst the insects are in the form of larval instars, pupal instars, or adult insects. The insects may, for example, be aphids, such as greenfly; whitefly, including glasshouse whitefly (*Trialeurodes vaporariorum*) and tobacco whitefly (*Bemisia tabacci*); or thrips, including Western flour thrips (*Frankliniella occidentalis*).

Although the mode of action of the liquid composition on insects is not known, it is thought that it may act to contain them in, for example, their eggs, larval instar form, pupae form, or restrain them in their adult form, having a mechanical effect such that the insects are physically hindered from developing and/or moving; and/or may act on the respiratory tract of the insects, perhaps by asphyxiation; and/or act by dehydration. However, it should be stressed that the action is clearly not that of a simple insect trap, such as a flypaper.

It should be stressed that the dextrinised starch material of the present invention is used as an active pesticidal agent.

The organisms may be mites (acarina), for example red spider, clover mites or broadmites in the form of adults or otherwise. Again, the mode of action is not known, although the mechanisms described above for insects may operate.

The organisms may be fungi, for example rusts or mildews, especially powdery mildews, including mildews of cereals. Again the mode of action is not known, although it may be a matter of mechanical containment, for example to prevent spores from bursting, or the provision of a barrier layer which prevents spores which land on a leaf from accessing the nutrients within the leaf, or which prevents spores from recognising the leaf as an acceptable host.

In general, therefore, it may be desirable in the method of the invention that the liquid composition is a somewhat sticky solution, either immediately upon application or after at least some curing/drying of the solution. However, it must again be emphasised that, whatever the mode of action, it is more subtle than to simply provide an insect trap of conventional type, in situ.

It is thought that if, indeed, the mode of action is not via a biochemical pathway but by a physical action, as suggested above, that the development of resistance by target organisms is unlikely to occur.

Since it is the chemical action of conventional pesticides which generate the selective pressure that gives rise to pest resistance, then it is probable that a change in the physical environment is far less likely to cause pest resistance. The enzymic mechanisms which enable pest resistance are not likely to overcome the new environmental conditions created by the use of dextrinised starch material as described herein.

The use of a naturally occurring material as an active pesticidal ingredient has obvious environmental attractions.

It should be appreciated that the dextrinised starch material is generally non-toxic. Accordingly, it may be advantageous to use the liquid compositions, in particular those in which the dextrinised starch material is the sole active ingredient, on edibles, for example, tomatoes, to combat tomato leaf minor, or in other cases where the use of potentially toxic pesticides may have detrimental and/or undesirable effects.

Where the dextrinised starch material is the sole active ingredient, there is little toxicological risk to the consumer of any food crop sprayed with the liquid composition. Similarly, since there may be no toxic residue, there is little chance of any detrimental effect to the wider environment, and its use is likely to be compatible with current biological control methods.

The method of the invention may be applied in an agricultural environment, or a horticultural environment, for example a glasshouse. The method is of particular interest to control pests in glasshouses.

The composition of the invention may include a foliar feed, and such a composition is particularly useful in a horticultural environment, especially a glasshouse.

The invention will now be described, by way of example.

Examples 1 to 8 relate to the use of a dextrin as the sole active ingredient in a biocidal composition. Examples 9 to 11 relate to the use of a dextrin in conjunction with other active ingredients.

EXAMPLE 1

Preparation of Biocidal Composition

A biocidal composition in accordance with the invention was prepared by mixing the following constituents:

AVEDEX 58 MD 14 C (Trade Mark) canary-yellow dextrin, derived from potato starch by acid pyrolysis (starch-pyrodextrin)—1.5%

0.2 wt % PBI SPREADER (Trade Mark) wetting agent (a nonyl phenol ethylene oxide condensate)

0.015 wt % sodium benzoate (preservative)

water to 100%

EXAMPLE 2

Activity against red spider mites (Tetranychus urticae)

Plants of Cucimus sativus c.v. Cillia were grown in liter pots in a greenhouse temperature set at 21° C.-26° C. to the first true leaf stage. Ten red spider mites (Tetranychus urticae) were introduced onto the first true leaf. Plants were sprayed using a domestic sprayer with the composition of Example 1 until the solution started to run off the leaf.

In a separate treatment, infected plants were sprayed with a 0.2 wt % solution of the wetting agent. In a third treatment an aqueous formulation was made up of 0.5 g/l of TORQUE (Trade Mark), a commercial formulation of fenbutatin oxide acaricide. In accordance with the manufacturer's instructions no wetting agent or preservative was added.

Replication was twenty fold and the pots were arranged in randomised blocks. The numbers of red spider mites were determined after 18 days.

The following Table 1 shows that the starch-dextrin solution was more effective than the commercial acaricide in killing red spider mites. It was possible to tentatively conclude that death was caused by physical means, for example, by asphyxiation, dehydration or by trapping or any combination of these processes.

TABLE 1

|  | Wetting Agent solution | Starch-dextrin solution | Fenbutatin oxide solution |
|---|---|---|---|
| Mean | 174.8 | 19.1 | 38.0 |
| Std error | 19.5 | 3.3 | 12.0 |

EXAMPLE 3

Activity against cucumber powdery mildew (Sphaeiotheca fuliginea)

Plants of Cucumis sativus c.v. Cillia, grown as described in Example 2, were inoculated with cucumber powdery mildew (Sphaeiotheca fuliginea) sixty minutes after the plants had been sprayed with the starch-dextrin solution of Example 1, the wetting agent solution described in Example 2, and a 0.025% solution of RUBIGAN (Trade Mark), a commercial fungicide, namely a fenamirol formulation. In accordance with the manufacturers instructions no wetting agent or preservative was added. The number of pustules was assessed after 10 days. Replication was twenty fold and the pots were arranged in randomised blocks.

Table 2 below shows that starch-dextrin was effective in reducing pustule formation by 57%, and spore germination was reduced on the leaves sprayed with starch-dextrin solution.

TABLE 2

|  | Wetting Agent solution | Starch-dextrin solution |
|---|---|---|
| Mean | 164.1 | 69.6 |
| Std error | 4.0 | 3.3 |

The fenarimol gave substantially 100% control.

Again, it may be tentatively concluded that control by the starch-dextrin solution was caused by a physical action.

EXAMPLE 4

Activity against Western flower thrips (Frankliniella occidentalis).

A substantial population of thrips was introduced to a large number of plants of Cucumis sativus c.v. Corona, on Day 1. The plants were sprayed to run off with the composition of Example 1, as described above, on Days 2 and 14. Thrip populations was assessed on Days 1, 3, 6, 9, 15 and 22, by sampling 70 leaves on each occasion. Total thrip population levels were as follows:

Day 1–74
Day 3–11
Day 6–35
Day 9–19
Day 15–6
Day 22–18

EXAMPLE 5

Activity against whitefly (Trialeurodes vaporariorum)

(a) Tests against scales (pupae)

Tobacco leaves heavily infested with whitefly scales were used for this test. Tobacco leaves were cut into squares, each infected with approximately 1000 scales. The following aqueous compositions were sprayed onto the leaves to run off:

|  | RESULT |
| --- | --- |
| Composition No. 1 0.2% wt PBI SPREADER | 0% death |
| Composition No. 2 2.5% wt AVEDEC | 8.3% death |
| Composition No. 3 2.5% wt AVEDEX + 0.2% wt PBI SPREADER | 29.9% death |
| Composition No. 4 5% wt AVEDEX | 26.9% death |
| Composition No. 5 5% wt AVEDEX + 0.2% wt PBI SPREADER | 18.5% death |

(b) Tests against eggs (b) Tobacco leaves heavily infested with whitefly eggs were used for this test. Tobacco leaves were cut into squares, each infected with approximately 600 eggs. Compositions Nos. 1 to 5 as described above were sprayed onto the leaves to run off, with the following results:

|  | RESULT |
| --- | --- |
| composition No. 1 | 0% death |
| Composition No. 2 | 85.8% death |
| Composition No. 3 | 94.7% death |
| Composition No. 4 | 95.5% death |
| Composition No. 5 | 98.4% death |

EXAMPLE 6

(Activity against Greenfly (*Aphids gossypii*

A simple test was carried out whereby an aqueous composition containing 0.5% wt AVEDEX and 0.1% wt PBI SPREADER was sprayed onto leaves of cucumber plants infested with greenfly. Visual inspection the following day indicated 100% death of the greenfly.

EXAMPLE 7

Activity against whitefly partially controlled by parasitic wasps (Encarsia)

It is believed that yellowing of plants is produced as a consequence of the presence of a pseudo best-yellows virus which is known to be transmitted by whitefly.

In an attempt to alleviate this problem, a biological control may be used, which control is aimed at killing the transmitters of disease, namely the whitefly. To this end, a defined amount of female parasite wasps are introduced into the greenhouse, which parasites parasitize larvae of the whitefly, eventually causing death to the whitefly. The new parasites are contained within whitefly pupae, in order to parasitize them. However, this method is not wholly effective and it would be desirable to use an additional form of control, which assisted the parasites in combating the whitefly whilst having no or a lesser detrimental effect on the parasites.

Experiments have shown that, employing treatments as described above, a substantial amount of new whitefly adults are contained, dead, in their respective pupae, unable to escape therefrom. In fact, in experiments, it has been noted that some of the adults show no signs of having broken through the cuticle of their pupae. Others are found to have partially broken through the cuticle but are unable to fully emerge from the pupae. It is thought that the starch-dextrin may mechanically inhibit the escape of the adult, which eventually dies from exhaustion, due to lack of essential nutrients which are not available within the pupae.

However, it has also been noted that the parasites are able to escape from the pupae in substantial number, apparently able to overcome any inhibition by the starch-dextrin. Whilst some adult parasites are killed, the overall effect of the composition was clearly in favour of the parasite.

EXAMPLE 8

Other Activity of the composition in Example 1

Activity has also been found against oat mildew.

Generally, tests against fungi have shown that a starch-dextrin solution has fungicidal effect when sprayed onto spores, or on to plant surfaces, such as leaves, later contacted by spores. In the former case, it may be that the mode of action is to inhibit bursting of spores, whilst in the latter, it may be that the starch-dextrin provides a barrier to a spore which has alighted on a leaf, thereby inhibiting its hyphae from "plugging into" the food channels of the leaf of the plant, the spore accordingly being unable to acquire any nutrients to provide energy for its germination, from the plant. It may also inhibit spore release and dispersal.

EXAMPLE 9

Activity against Broadmites

Five labelled cucumber leaves infected with Broadmite were sprayed, using a domestic sprayer, with the following aqueous compositions:

Composition No. 1—an aqueous formulation made up of 0.5 g/l of TORQUE (Trade Mark for a wettable powder containing 50 wt % of the active ingredient fenbutin oxide).

Composition No. 2—an aqueous solution made up of 1.0 g/l of TORQUE.

Composition No. 3—an aqueous solution made up of 1.5 wt % of AVEDEX 58 MD 14 C as described in Example 1 and 1 ml/l of PBI SPREADER.

Composition No. 4—an aqueous solution made up of 1.5 wt % AVEDEX 58 MD 14 C, 1 ml/l of PBI SPREADER and 0.5 wt % of TORQUE.

Composition No. 5—an aqueous solution made up of 1.5 wt % AVEDEX 58 MD 14 C, 1 ml/l of PBI SPREADER and 1.0 wt % of TORQUE.

Results

Compositions 1, 2 and 3 had no significant effect on the Broadmites. Compositions 4 and 5 left large numbers of Broadmites dead. There was no observable difference in effect between Compositions 4 and 5. This result led to a large scale spray of composition of Example 1 which after three sprays produced control of the pest.

EXAMPLE 10

Activity against Cucumber Powdery Mildew (*Sphaertheca fuligines*)

Plants of Cucumis sativus c.v. Cillia were grown in liter pots in a glasshouse temperature set at 21° C. to 26°C. When the fifth true leaf was approximately 3 inches in diameter the plants were infected with cucumber powdery mildew (*Sphaeiothea fulginea*) by shaking a heavily infected leaf over each plant. Sixty minutes before infection, the plants were sprayed with one of the aqueous compositions noted in the table below to run off, using a domestic sprayer. Each plant received approximately 40 ml of the solution.

There were six plants per treatment and the plants were arranged in randomised blocks. After seven days, the proportion of the fifth true leaf infected with mildew pustules was estimated and recorded. The results are recorded in the table below. CODICIDE (Trade Mark) noted in the table is a commercially available vegetable oil

|  | Constituents | Mean % of fifth true leaf with powdery mildrew |
|---|---|---|
| Composition No. 1 | Water | 90.0 |
| Composition No. 2 | 0.2 ml/l RUBIGAN | 24.1 |
| Composition No. 3 | 0.2 ml/l CODICIDE + 0.2 ml/l RUBIGAN | 86.2 |
| Composition No. 4 | 1.5 wt % AVEDEX + 1 ml/l PBI SPREADER | 42.7 |
| Composition No. 5 | 1.5 wt % AVEDEX + 0.2 ml/l RUBIGAN | 7.6 |
| Composition No. 6 | 0.75 wt % AVEDEX + 0.2 ml/l RUBIGAN | 14.5 |
| Composition No. 7 | 0.015 wt % AVEDEX + 0.2 ml/l RUBIGAN | 14.5 |
| Composition No. 8 | 0.0015 wt % AVEDEX + 0.2 ml/l RUBIGAN | 17.6 |

It should be noted from the results that the compositions numbered 5 to 8 provide the most effective treatment and that each of these compositions includes AVEDEX and a commercial fungicide RUBIGAN (Trade Mark for a commercial formulation containing the active ingredient Fenarimol. The formulation is a suspension concentrate containing 12 wt % of active ingredient). The compositions numbered 5 to 8 are more effective than compositions containing AVEDEX alone (Composition No. 4) or RUBIGAN alone (Composition No. 2).

EXAMPLE 11

Activity against Western-flower Thrips (*Frankliniella occidentalis*)

Five leaves on two cucumber plants grown in rockwool were selected and labelled for treatment with each composition described below. The number of Western flower thrip larvae was determined and recorded. The plants and their two immediate neighbours were sprayed with 0.25 liters of one of the aqueous compositions noted in the table below. The compositions were applied to plants in the same glasshouse within an area of 250 m², the treated plants being 2.5 m² apart. The spray was applied using a domestic sprayer. Twenty-four hours after application of the spray the number of surviving thrip larvae was determined. AFUGAN (Trade Mark) referred to in the table below is a commercial carboxylic acid ethyl ester containing 30 wt % of active ingredient as an emulsifiable concentrate.

| Composition No. 1 | 0.5 ml/l AFUGAN |
| Composition No. 2 | 1.0 ml/l AFUGAN |
| Composition No. 3 | 1.5 wt % AVEDEX + 0.5 ml/l AFUGAN |
| Composition No. 4 | 0.75 wt % AVEDEX + 0.5 ml/l AFUGAN |
| Composition No. 5 | 0.015 wt % AVEDEX + 0.5 ml/l AFUGAN |
| Composition No. 6 | 0.0015 wt % AVEDEX + 0.5 ml/l AFUGAN |
| Composition No. 7 | 1.5 wt % AVEDEX + 1 ml/l AFUGAN |

Results are shown in the table below. The data refers to the number of thrip larvae before spraying; the number surviving after spraying; and the percentage thrip larvae surviving after spraying.

|  | Before spray | After spray | % thrip larvae surviving |
|---|---|---|---|
| Composition No. 1 | 42 | 18 | 51.9 |
|  | 35 | 26 |  |
|  | 58 | 24 |  |
|  | 93 | 68 |  |
|  | 98 | 35 |  |
| Composition No. 2 | 48 | 3 | 14.6 |
|  | 37 | 3 |  |
|  | 127 | 18 |  |
|  | 86 | 22 |  |
|  | 58 | 6 |  |
| Composition No. 3 | 73 | 3 | 7.7 |
|  | 47 | 6 |  |
|  | 70 | 7 |  |
|  | 95 | 7 |  |
|  | 88 | 6 |  |
| Composition No. 4 | 132 | 12 | 5.8 |
|  | 35 | 3 |  |
|  | 68 | 3 |  |
|  | 72 | 2 |  |
|  | 34 | — |  |
| Composition No. 5 | 76 | 11 | 10.0 |
|  | 40 | 7 |  |
|  | 46 | 2 |  |
|  | 87 | 8 |  |
|  | 32 | — |  |
| Composition No. 6 | 48 | 21 | 21.3 |
|  | 46 | 9 |  |
|  | 54 | 4 |  |
|  | 97 | 21 |  |
|  | 23 | 2 |  |
| Composition No. 7 | 78 | 10 | 9.0 |
|  | 49 | 7 |  |
|  | 62 | 6 |  |
|  | 68 | 3 |  |
|  | 32 | — |  |

I claim:
1. A method of treatment of a plant to combat an undesired insect, mite or fungal organism which is infecting the plant or may subsequently infect the plant, comprising the step of foliar application of a liquid composition comprising, as an active ingredient, a dextrinised starch material.
2. A method as claimed in claim 1, wherein the active ingredient is a pyrodextrin derived from starch or amylopectin.
3. A method as claimed in claim 2, wherein the active ingredient is a pyrodextrin derived by spraying starch, or amylopectin with an acid, drying the acidified material to leave a water content of 1-5 wt %, hydrolyzing the acidified and dried material, and subjecting it to a temperature of 150°-180° C.
4. A method as claimed in claim 1, wherein the active ingredient is derived from tubers or cereals.
5. A method as claimed in claim 4, wherein the active ingredient is derived from potatoes.
6. A method as claimed in claim 1, wherein the dosage of dextrinised starch material is 50-150 kg/ha.
7. A method according to claim 1, wherein said liquid composition comprises 0.05 to 5 weight percent of a wetting agent.
8. A method according to claim 1, wherein a foliar feed is present.
9. A method as claimed in claim 1, wherein the liquid composition includes a further active ingredient.
10. A method as claimed in claim 9, wherein the further active ingredient is a synthetic chemical pesticidal agent.

11. A method as claimed in claim 10, wherein the liquid composition includes hexakis (2-methyl-2-phenylpropyl)distannoxane), as a further actitve ingredient.

12. A method as claimed in claim 10, wherein the liquid composition includes alpha-(2-chlorophenyl)-alpha-(4-chlorophenyl)-5-pyrimidinemethanol) as a further active ingredient.

13. A method as claimed in claim 10, wherein the liquid composition includes 2-((Diethoxyphosphinothioyl)oxy)-5-methylpyrazolo(1,5-a)pyrimidine-6-carboxylic acid ethyl ester as an active ingredient.

* * * * *